(12) United States Patent
Hyde et al.

(10) Patent No.: US 11,266,797 B2
(45) Date of Patent: Mar. 8, 2022

(54) COLLAPSIBLE, DISPOSABLE MEDICATION INHALATION SPACER AND METHOD

(71) Applicant: THAYER MEDICAL CORPORATION, Tucson, AZ (US)

(72) Inventors: Joel Hyde, Tucson, AZ (US); Jennifer Johnson, Tucson, AZ (US)

(73) Assignee: THAYER MEDICAL CORPORATION, Tucson, AZ (US)

( * ) Notice: Subject to any disclaimer, the term of this patent is extended or adjusted under 35 U.S.C. 154(b) by 210 days.

(21) Appl. No.: 16/368,581

(22) Filed: Mar. 28, 2019

(65) Prior Publication Data

US 2020/0306467 A1 Oct. 1, 2020

(51) Int. Cl.
*A61M 15/00* (2006.01)

(52) U.S. Cl.
CPC ...... *A61M 15/0088* (2014.02); *A61M 15/009* (2013.01); *A61M 15/0021* (2014.02); *A61M 15/0028* (2013.01)

(58) Field of Classification Search
CPC ...... A61M 11/00; A61M 11/02; A61M 11/06; A61M 11/08; A61M 15/00; A61M 15/0013; A61M 15/0016; A61M 15/0018; A61M 15/0021; A61M 15/0086–0088; A61M 15/009
See application file for complete search history.

(56) References Cited

U.S. PATENT DOCUMENTS

| | | | |
|---|---|---|---|
| 4,951,661 A | 8/1990 | Sladek | 128/202.27 |
| 4,953,545 A | 9/1990 | McCarty | 128/200.23 |
| D335,175 S | 4/1993 | Sladek | D24/110 |
| 5,427,089 A | 6/1995 | Kraemer | A61M 11/00 |
| D362,500 S | 9/1995 | Cook et al. | D24/110 |
| 5,474,058 A | 12/1995 | Lix | 128/200.18 |

(Continued)

FOREIGN PATENT DOCUMENTS

| | | | |
|---|---|---|---|
| CA | 2212642 | 8/1996 | A63B 23/18 |
| CA | 2223518 | 12/1996 | A63B 23/18 |

(Continued)

OTHER PUBLICATIONS

Notice of Allowance issued in U.S. Appl. No. 16/368,585, dated Nov. 14, 2019 (9 pgs).

(Continued)

*Primary Examiner* — Rachel T Sippel
(74) *Attorney, Agent, or Firm* — Hayes Soloway P.C.

(57) ABSTRACT

A medication inhalation apparatus includes an outer housing, movable between collapsed and expanded states, encompassing a first volume. An inner housing within the outer housing encompasses an inner volume. An inhaler opening to the first volume is within a wall of the outer housing at a first location. A mouth opening to the inner volume is within a wall of the outer housing and the inner housing at a second location. A one-way inhalation valve connecting the first volume and the inner volume is within a wall of the inner housing. A one-way exhalation valve connecting the inner volume and the exterior of the outer housing is within a wall of the outer housing and inner housing at a third location. In the expanded state, gas flows from the inhaler to the first volume, the first volume to the inner volume, and the inner volume to a user's mouth.

13 Claims, 8 Drawing Sheets

(56) References Cited

U.S. PATENT DOCUMENTS

| | | | |
|---|---|---|---|
| 6,014,972 A | 1/2000 | Sladek | 128/203.12 |
| 6,039,042 A | 3/2000 | Sladek | A61M 11/00 |
| 6,098,619 A | 8/2000 | Britto et al. | A61M 11/003 |
| 6,202,643 B1 | 3/2001 | Sladek | 128/200.23 |
| 6,435,176 B1 | 8/2002 | Berg et al. | 128/200.23 |
| 6,463,929 B1 | 10/2002 | Scheuch | A61M 15/00 |
| 6,550,473 B1 | 4/2003 | Sladek | 128/200.23 |
| 6,679,252 B2 | 1/2004 | Sladek | 128/200.23 |
| 7,347,203 B2 | 3/2008 | Marler et al. | 128/201.13 |
| 7,360,537 B2 | 4/2008 | Snyder et al. | 128/200.23 |
| 7,921,846 B1 | 4/2011 | Marler et al. | 128/205.24 |
| 2002/0129814 A1 | 9/2002 | Sladek | A61M 11/00 |
| 2009/0032019 A1 | 2/2009 | Green et al. | A61M 15/0086 |
| 2010/0163045 A1 | 7/2010 | Powell et al. | A61M 11/00 |
| 2013/0276781 A1 | 10/2013 | Steelman | A61M 15/0023 |
| 2016/0045686 A1 | 2/2016 | Jaroslavsky | A61M 15/0088 |
| 2019/0151578 A1 | 5/2019 | Dennis | A61M 15/0088 |
| 2019/0231994 A1 | 8/2019 | Jaroslavsky | A61M 15/0086 |
| 2019/0358415 A1* | 11/2019 | Taghavi | A61M 15/0021 |
| 2020/0282158 A1* | 9/2020 | Friel | A61M 15/0086 |

FOREIGN PATENT DOCUMENTS

| | | | |
|---|---|---|---|
| EP | 1204437 | 2/2005 | A61M 11/04 |
| WO | WO 96/37249 | 11/1996 | A61M 15/00 |
| WO | WO2017205907 | 12/2017 | A61M 15/00 |
| WO | WO 2017205907 | 12/2017 | A61M 15/00 |
| WO | WO2019007968 | 1/2019 | A61M 15/00 |

OTHER PUBLICATIONS

Australian Certificate of Registration of Trademark, No. 1751570 for LITEAIRE, filed Feb. 10, 2016 (1 pg).

LiteAire® sales literature, downloaded from http://thayermedical.com on Apr. 18, 2019 (20 pgs).

Office Action issued in U.S. Appl. No. 16/368,585, dated Jul. 31, 2019 (16 pgs).

International Search Report and Written Opinion issued in related PCT International Patent Application Serial No. PCT/US20/25714, dated Aug. 12, 2020 (14 pages).

Invitation to Pay Additional Fees issued in related PCT International Patent Application Serial No. PCT/US20/25714, dated Jun. 17, 2020 (2 pages).

U.S. Appl. No. 16/368,585, filed Mar. 28, 2019.

International Preliminary Report on Patentability issued in related PCT International Patent Application Serial No. PCT/US20/25714, dated Oct. 7, 2021 (11 pages).

Office Action issued in U.S. Appl. No. 16/777,529, dated Dec. 6, 2021 (14 pgs).

* cited by examiner

Method of expanding a medication inhalation apparatus from an initially flat, collapsed state

610 — Providing, in the collapsed state, an outer housing, an inner housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location;

620 — Pressing a pair of opposite sidewall panels on the outer housing;

630 — Manually expanding the outer housing and inner housing to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a patient.

FIG. 6

COLLAPSIBLE, DISPOSABLE MEDICATION INHALATION SPACER AND METHOD

FIELD OF THE DISCLOSURE

The present disclosure is generally related to aerosol medication inhalers and more particularly is related to valved chambers for delivering aerosol medication from an MDI canister.

BACKGROUND OF THE DISCLOSURE

Pressurized Metered Dose Inhaler (MDI) canisters, which have been used since 1956, ordinarily are sold with a dispenser or so-called "boot" that includes an actuator, a nozzle, and a mouthpiece. The user can self-administer the MDI medicament using the boot alone; however, the user must place the mouthpiece of the boot in or near his/her mouth and inhale at essentially the same time the MDI canister is actuated. Some users, like young children and the elderly, find it difficult to coordinate their inhalation with the actuation of the MDI, and even if the user is able to coordinate their inhalation with MDI inhalation, a lot of medicament is deposited into the oropharynx, leading to undesirable side-effects, such as hoarseness or thrush when using corticosteroids.

At first, "Spacers" were created to address the undesirable oropharyngeal deposition; however, these devices do not address the need for coordinated breathing technique. Medical device manufacturers have since created valved holding chambers (VHCs) to address both issues. To combat oropharyngeal deposition, VHCs (like spacers) have a chamber that holds the aerosol plume. This chamber lets the aerosol plume decelerate giving medicament particles the volume needed to aerosolize, and it allows particles that would normally impact on the user's oropharynx to deposit on the inside of the chamber instead. To help alleviate issues with the synchronization of a user's breath with MDI actuation, VHCs also employ a valving system that permits the user's inhalation to draw the medicament from the chamber but re-directs the user's exhalation to be vented out of the mouthpiece of the VHC such that the remaining aerosolized medicament inside the chamber is not blown backwards out of the chamber. This allows patients who can't synchronize their inhalation with MDI actuation to get a significant dose of medicament. It also allows the patient to continue breathing through the VHC throughout the treatment, as the presence of the exhalation valve means there is no need to remove the VHC from the patient's mouth during exhalation. Ultimately, the patient can take in the full dose, while breathing as normally as possible, over multiple breaths if necessary. These devices have now become the recommended as the best-practice accessory to an MDI for patients of all ages.

Many commercially available VHCs, like the Aerochamber Plus® Z-Stat® device available from Monaghan Medical Corporation, and Optichamber® Diamond device available from Philips Respironics, are made of rigid plastic and are substantially cylindrical in shape with a diameter of a couple inches and a length of roughly half a foot, which presents problems to users that need to carry MDI canisters with them all day in case of an emergency asthma attack. Also, in facilities that store large numbers of holding chambers, like hospitals or spirometry testing facilities, the cylindrical shape of most VHCs means that the storage of many VHCs takes up a significant amount of space. Some VHC manufacturers have identified these issues and have partially addressed them by creating collapsible cylindrical VHCs. Many of these collapsible VHCs, however, don't offer a significant advantage to a non-collapsible chamber. For example, the BreatheRite™ collapsible device available from Medline Industries, Inc., shortens the length of the device by a couple inches when collapsed, but the device is still a rigid cylinder with the same diameter. The cylindrical shape still means that the device can't fit comfortably in a user's pocket, as well as meaning that storing large quantities of these devices would still take large amounts of space. The Thayer Medical LiteAire® spacer device collapses to a substantially flat configuration and the dimensions of the VHC allow the device to be carried unobtrusively in a shirt pocket or purse. Also, many LiteAire® spacer devices can be stored in a relatively small area because the packaged devices can be stacked flat on top of each other with very little empty space between devices, which is not possible with cylindrically shaped devices like the BreatheRite™ collapsible device.

Conventional VHCs, like the Aerochamber Plus® Z-Stat® device and Optichamber® Diamond device, cost in the range of $10-20. Some medical applications, like spirometry testing, only require a VHC to be used during a brief testing period by a patient, and this price offers a barrier to the use of a VHC in these settings. While lower cost plastic VHCs have recently been introduced to the market, the recent awareness of the need for environmental sustainability identified another problem with the rigid cylindrical plastic solution. Plastic taxes the environment when disposed of with the frequency required in higher-usage clinical environments like spirometry testing facilities. The LiteAire® offers a solution to this problem as well, with 98% of the device being made from paperboard, the environmental impact upon disposal of the device is substantially reduced.

Another benefit of the LiteAire®'s collapsible device construction is that the device is made of a paperboard which is inherently an antistatic material. The fact that the traditional plastic construction of other VHCs creates a large amount of medicament deposition due to static build up on the inside surface of the VHC has been established by multiple sources, including some patents. Multiple patents have been filed for VHCs or spacers made from antistatic materials. For example, U.S. Pat. Nos. 6,435,176 and 7,360,537, which describe devices made from metal and antistatic plastic, respectively, seek to address this problem. These patents offer solutions to electrostatic deposition but run into some of the same rigidity, cost, and disposal problems mentioned above; and they remain bulky and/or expensive. The LiteAire® collapsible device is able to reduce electrostatic deposition as well as being inexpensive, easily portable and environmentally friendly.

While the LiteAire already offers an inexpensive, disposable, collapsible, and antistatic VHC, additional features are still possible. The current iteration of the LiteAire requires the user or caregiver to pinch the sides of the barrier wall during the process of administering the dose of medicament. Anytime a use detail such as this is conveyed in the instructions (also known as a labeling control), if it can affect dose delivery, a design control is preferred. The more intended and reproducible medicament delivery is dependent upon the device design (not on the user), the better.

Further advantage can be gained by achieving near totality of the separation between the chamber holding the aerosolized medicament and the mouthpiece section without the assistance of the user's "pinch". As such, a redesign of the mouthpiece configuration can do away with any holding requirement for the user by disabling any effect the user's exhaled breath might otherwise have on aerosol plume in the chamber.

The present application addresses these potential variants in the LiteAire design. These variants would continue to provide the same advantages that the LiteAire already offers over the prior art discussed above and would supplement those advantages.

SUMMARY OF THE DISCLOSURE

Accordingly, it is an object of the invention to improve the efficiency of a collapsible/expandable valved chamber device for delivering MDI medications for the like.

It is another object of the invention to reduce the amount of MDI medication lost from a user exhaling into the chamber by preventing a user using a collapsible/expandable valved chamber from inadvertently blowing MDI medication out of the collapsible/expandable valved chamber if the user inadvertently exhales while actuating an MDI canister that introduces the medication into the collapsible/expandable valved chamber, or the user takes in the dose over multiple breaths.

It is another object of the invention to provide an inexpensive, disposable, collapsible valved chamber for delivering MDI medications or other inhaled treatments.

It is another object of the invention to provide an inexpensive, disposable valved chamber which is collapsible to a flat configuration.

It is another object of the invention to provide a valved chamber which is sufficiently inexpensive that it can be used as a discardable diagnostic dosing aid, temporary medication delivery aid, or training aid by means of which a health care provider can demonstrate proper techniques for using a permanent valved chamber.

It is another object of the invention to provide a valved chamber which can pop up from a collapsed configuration to an expanded configuration ready for use.

It is another object of the invention to provide a valved chamber which can pop up from a collapsed configuration to an expanded configuration ready for use and retain the expanded configuration.

It is another object of the invention to provide a valved chamber which can be "popped up" or erected from a collapsed configuration by a user with a minimal amount of effort.

The present disclosure can be viewed as providing a medication inhalation apparatus. Briefly described, in architecture, one embodiment of the system, among others, can be implemented as follows. The apparatus includes an outer housing collapsible into a substantially flat configuration and expandable to bound a first volume adapted to receive a plume of medication particles ejected by an MDI inhaler.

The apparatus also includes a fully contained inner housing also collapsible into a substantially flat configuration, located within the outer housing and expandable to bound a second volume. A first opening is formed through a wall of the outer housing at a first location, in fluid communication with the first volume, and adapted to accommodate a mouthpiece of an MDI inhaler. Second and third openings are formed through walls of the outer housing and the inner housing adapted to form an user mouth opening in fluid communication with the second volume. A one-way inhalation valve is located within a wall of the inner housing. The inhalation valve connects the first volume and the second volume. A one-way exhalation valve is located within a wall of the outer housing and the inner housing. The exhalation valve connects the inner volume and the exterior of the outer housing. When the apparatus is in an expanded state, gas is flowable from a connected MDI to the first volume, from the first volume to the second volume, and from the inner volume to the mouth of a user.

The present disclosure can also be viewed as providing methods of expanding a medication inhalation apparatus from an initially flat, collapsed state to an expanded state by providing a medication inhalation apparatus as above described, and manually pressing a pair of opposite sidewall panels on the outer housing towards one another, whereby to force the opposite sidewall panels into positions approximately perpendicular to top and bottom panels of the outer housing, and inserting a mouthpiece of an MDI inhaler into an inhaler opening in the outer housing, whereupon the apparatus is ready for use by a patient.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6 is a flowchart describing a method of expanding a medication inhalation apparatus from an initially flat, collapsed state, in accordance with a first embodiment of the present disclosure.

DETAILED DESCRIPTION

Figure 1A:
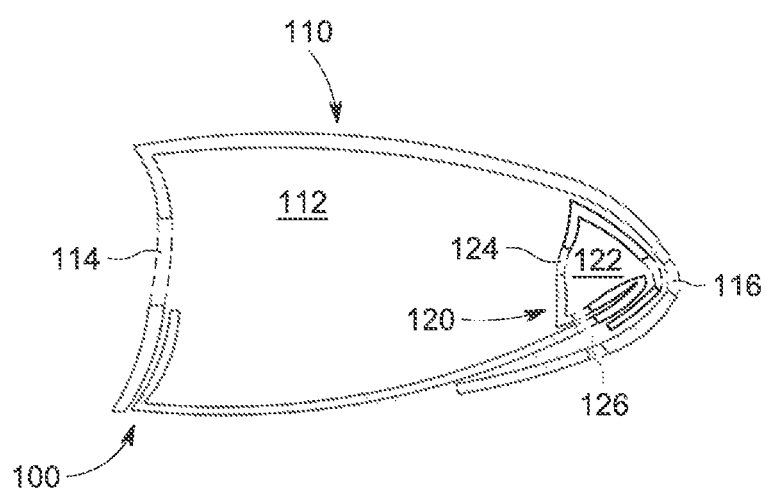
FIG. 1A is a longitudinal cross-sectional view of the apparatus in an expanded state, in accordance with a first exemplary embodiment of the present disclosure.

FIG. 1A is a longitudinal cross-sectional view of the apparatus 100 in an expanded state, in accordance with a first exemplary embodiment of the present disclosure. The apparatus 100 includes an outer housing 110, movable between a collapsed state and an expanded state. The collapsed state has a substantially flat configuration. The expanded state encompasses a first volume 112. The apparatus also includes an inner housing 120 positioned within the outer housing 110 and encompassing an inner volume 122. Housing 110 has perforations on the side and openings on the side that render it not airtight. Housing 120 has holes at the corners. The interface between volume 122 and 112 is the substantially airtight portion.

An inhaler opening 114 is formed at least partially within a sidewall of the outer housing 110 at a first location. The inhaler opening 114 is in fluid communication with the first volume 112, and the mouthpiece of a metered dose inhaler (see FIG. 3) can be inserted within the inhaler opening 114. A mouth opening 116 is positioned within a sidewall of the outer housing 110 and the inner housing 120 at a second location. The mouth opening 116 is in fluid communication with the inner volume 122. A one-way inhalation valve 124 is positioned within a sidewall of the inner housing 120. The inhalation valve 124 connects the first volume 112 and the inner volume 122. A one-way exhalation valve 126 is positioned within a sidewall of the outer housing 110 and the inner housing 120 at a third location. The exhalation valve 126 connects the inner volume 122 and the exterior of the outer housing 110. When the apparatus 100 is in an expanded state, gas is flowable from the metered dose inhaler to the first volume 112, from the first volume 112 to the inner volume 122, and from the inner volume 122 to the mouth of a user. In the expanded state, gas is also flowable from the mouth of a user to the inner volume 122 and to the exterior of the outer housing 110.

Figure 1B:
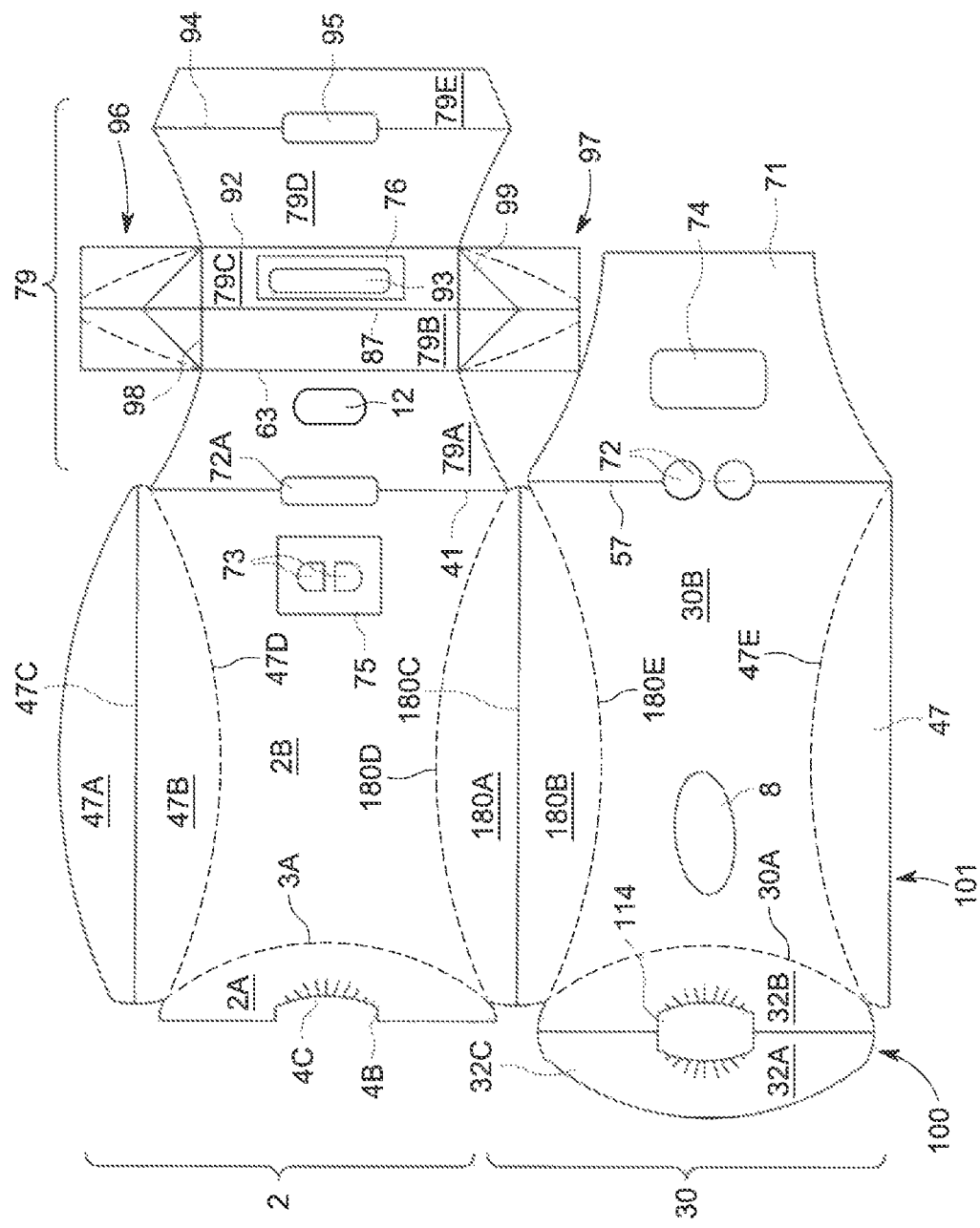
FIG. 1B is a plan view of a sheet from which the apparatus is constructed, in accordance with a first exemplary embodiment of the present disclosure.

FIG. 1B is a plan view of a sheet 101 from which the apparatus 100 is constructed, in accordance with a first exemplary embodiment of the present disclosure. The sheet 101, when assembled, pops up into the expanded state shown in FIG. 1A. FIG. 1B shows the exterior side of the sheet 101, i.e., the side that forms the exterior of the apparatus 100 as assembled. Sheet 101 includes a bottom section 2, a top section 30, an inner housing section 79, and an outer mouthpiece section 71. The inner housing 120 is formed from the panels in the inner housing section 79, while the outer housing 110 is formed from the remaining portions of the sheet 101. The bottom section 2 and top section 30 are connected by a right side section, which includes two right side panels 180A and 180B connected by a straight scored fold line 180C as shown. Right side panel 180A is connected along an arcuate "skip-scored" or perforated fold line 180D to bottom panel 2B, and right side panel 180B is connected along an arcuate skip-scored fold line 180E to top panel 30B. (A skip-scored fold line includes a sequence of scored and non-scored sections of a fold line having the appearance of dashed line).

On the top section 30, adhesive attachment panel 47 is connected by an arcuate scored or perforated fold line 47E to top panel 30B, and eventually is adhesively attached to the inner surface of left side panel 47A on bottom section 2. Left side panel 47A is connected to panel 47B, which is connected to bottom panel 2B by arcuate fold line 47D.

In one example, top panel 30B may have a window opening 8 therein, with a piece of transparent membrane adhesively attached to the inner surface of top panel 30B source to provide a sealed, transparent window into the interior of valved chamber 1A. In another example, the apparatus 100 may have no viewing window.

On the bottom section 2, the rear end portion of bottom panel 2B is connected along an arcuate skip-scored fold line 3A to an inner boot adapter panel 2A. Conversely, on the top section 30, an outer boot adapter panel 32A,B includes a panel 32A which is connected along a straight scored fold line 32C to an outer boot adapter panel 32B, which is connected along arcuate skip-scored fold line 30A to the rear end of top panel 30B. A portion of an elongated inhaler opening 114 bounded by scalloped sections 4B, which are formed by slits 4C, is aligned with a corresponding portion of half-opening 4B in inner boot adapter panel 2A.

Outer mouthpiece section 71 is connected along straight scored fold line 57 to top panel 30B. Circular openings 72 may be symmetrically formed in both top panel 30B and outer mouthpiece section 71, so as to be bisected by scored fold line 57. In another example, openings 72 may be any suitable shape, such as square, rectangle, oval, and the like. In another example, openings 72 may be located at any suitable point along top panel 30B. For instance, openings 72 may be exclusively located on top panel 30B or exclusively located on mouthpiece section 71. Or, openings 72 may be asymmetrically formed in both top panel 30B and mouthpiece section 71.

In one example, exhalation valve 126 (shown in FIG. 1A) may be formed on bottom section 2. A pair of exhalation valve openings 73 may be formed in bottom panel 2B, with an exhale membrane 75 attached along one side of exhalation valve openings 73 so as to cover them, and to flex away from exhalation valve openings 73 when a user exhales into inner volume 122 of inner housing 120. This allows exhaled breath to be exhausted through exhalation valve openings 73, and to seal them closed when the user inhales through openings 72.

Inner housing section 79 includes an elongated, trapezoidal panel 79A connected along straight scored fold line 41 to bottom panel 2B and a rectangular panel 79B connected along a straight scored fold line 63 to panel 79A. An elongated opening 12 in panel 79A becomes aligned with exhalation valve openings 73 when panel 79A is folded against the inner surface of bottom panel 2B as shown in FIG. 1A. When assembled, the portion of the apparatus 100 wherein opening 72A is located may be the mouth opening side of the apparatus 100. Outer mouthpiece section 71 also includes an opening 74 configured to overlie exhalation valve openings 73 when the apparatus is assembled and expanded for use.

In one example, an elongated rectangular opening 72A is symmetrically formed in bottom panel 2B and panel 79A so as to be bisected by fold line 41. Opening 72A may be any suitable shape to work in conjunction with openings 72. Opening 72A may comprise one or more openings to work in conjunction with openings 72. Opening 72A may be located at any point on bottom panel 2B or panel 79A to work in conjunction with openings 72. For instance, depending on the location of openings 72, opening 72A may be located entirely on bottom panel 2B, entirely on panel 79A, or asymmetrically formed within both bottom panel 2B and panel 79A.

Panel 79B is connected to another panel 79C along a straight scored fold line 87. A rectangular inhalation valve opening 93 is formed centrally in panel 79C. A rectangular inhalation membrane 76 is adhesively attached to the outer surface of the sheet 101 so as to cover inhalation valve opening 93 and flex to uncover inhalation valve opening 93 as the user inhales through openings 72 and 72A. Also, the opening of the flap necessarily causes a change in airflow direction, which has been shown to be advantageous in further reducing CPD in some papers. Panel 79E may be adhesively connected to the exterior of panel 2B upon assembly.

Panel 79C is attached to trapezoidal panel 79D along a straight skip-scored fold line 92. Preferably, inhalation valve opening 93 is as large as can be practically fit into panel 79C while nevertheless providing adequate room both for attachment of inhalation membrane 76 to panel 79C and for proper operation of inhalation membrane 76.

Trapezoidal panel 79E is connected to panel 79D along a continuously scored fold line 94. In one example, opening 95 is located symmetrically between panels 79D and 79E.

Side panels 96 and 97 are connected to panels 79B and 79C along straight, continuously-scored fold lines 98 and 99. Side panels 96 and 97, which are unique to the instant invention, and make the interface between the first volume 112 and the inner volume 122 substantially air tight, and which differentiate the instant apparatus from the LiteAire® device and apparatus disclosed in prior U.S. Pat. No. 6,679,252, are discussed in greater detail in FIG. 2, below.

It should be noted that all openings may have any size, shape, orientation, number, and placement suitable to work in conjunction with each other and to facilitate use by a user. FIGS. 1A and 1B show exemplary openings generally located centrally on the apparatus 100.

Figure 2:
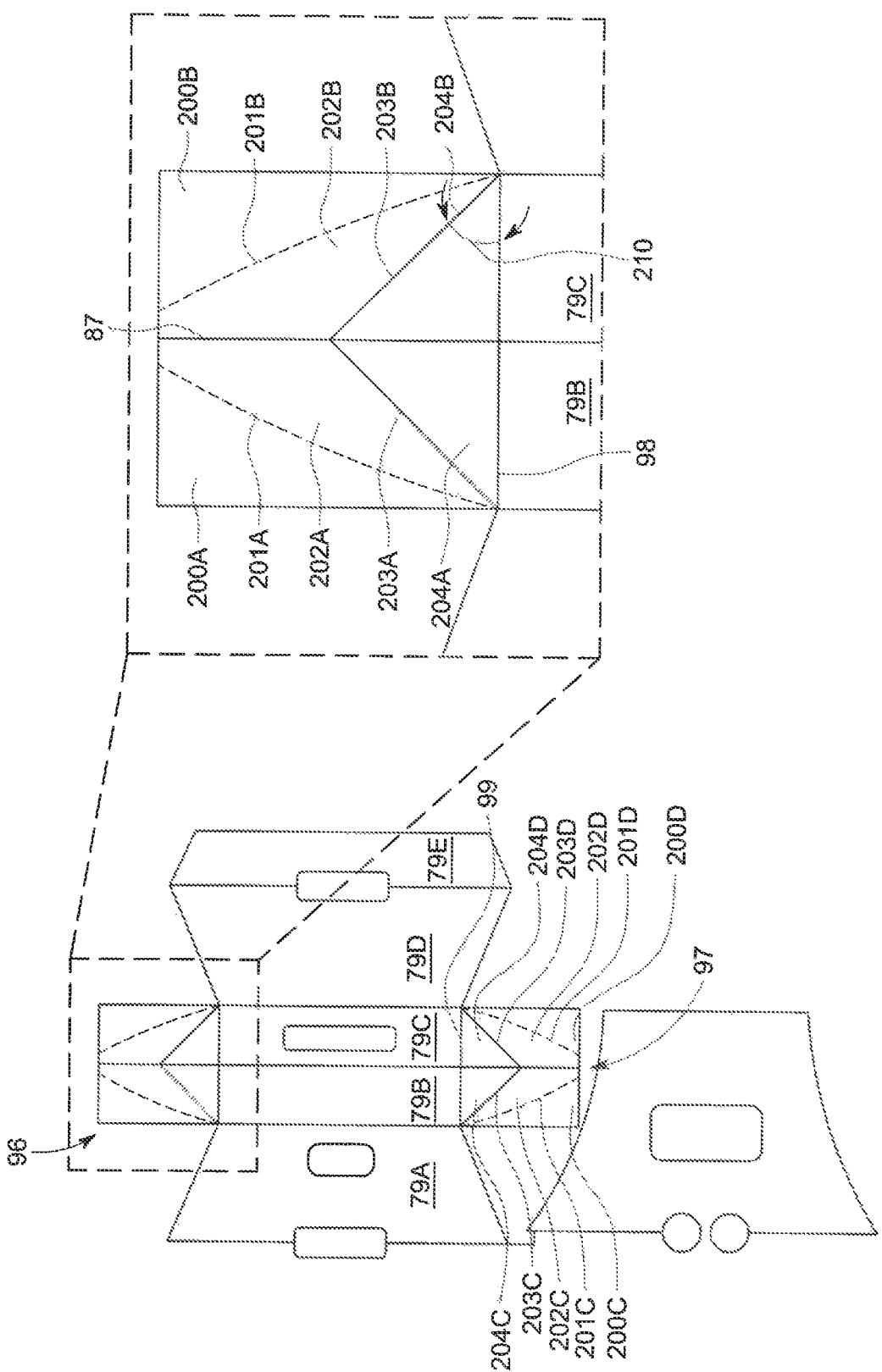
FIG. 2 is a close-up plan view of the sheet of FIG. 1B, in accordance with a first exemplary embodiment of the present disclosure.

FIG. 2 is a close-up plan view of the sheet 101 of FIG. 1B, in accordance with a first exemplary embodiment of the present disclosure. FIG. 2 shows the portion of the sheet 101 that, when assembled, forms the inner housing 120 of FIG. 1A. Panels 79A-E are shown connected by score lines. Connected to panels 79B and 79C are side panels 96 and 97. In the example shown in FIG. 2, side panels 96 and 97 are the same design on opposite sides of side panels 79B and 79C. Left and right sides of side panels 96 and 97 are also symmetrical about line 87.

Side panel 96 is shown within the close-up inset. Side panel 96 is a shown as a rectangular panel comprising several flaps differentiated by diagonal scoring or perforation lines. On the left side, flaps 200A and 202A are differentiated by skip-scored fold line 201A. Flaps 202A and 204A are differentiated by perforation or scored line 203A. And flap 204A is differentiated from panel 79B by continuous score line 98. On the right side, flaps 200B and 202B are differentiated by skip-scored fold line 201B. Flaps 202B and 204B are differentiated by perforation line 203B. And flap 204B is differentiated from panel 79C by continuous score line 98. In one example, the angle 210 between score line 98 and perforation lines 204A or 204B may be 45°. The angle 210 may be more or less depending on the size and shape of the flaps.

Side panel 97 comprises reciprocal flaps differentiated by diagonal scoring or perforation lines. On the left side, flaps 200C and 202C are differentiated by skip-scored fold line 201C. Flaps 202C and 204C are differentiated by perforation line 203C. And flap 204C is differentiated from panel 79B by continuous score line 99. On the right side, flaps 200D and 202D are differentiated by skip-scored fold line 201D. Flaps 202D and 204D are differentiated by perforation line 203D. And flap 204D is differentiated from panel 79C by continuous score line 99. In one example, the angle between score line 99 and perforation lines 204C or 204D may be 45°. The angle may be more or less depending on the size and shape of the flaps.

The left and right sides of side panels 96 and 97 are differentiated by continuous score line 87, which runs from side panel 96, between panels 79B and 79C, and through side panel 97. Each of the score or perforation lines 201A-D, 203A-D, 98, 99 runs from a point along line 87 to an outer corner of the side panel 96, 97.

When assembled, the side panels 96, 97 fold inward to create an inner housing 120. The side panels 96, 97 become sidewalls for the housing 120. While the chamber itself is not airtight, the interface between the inner volume and the outer volume is substantially airtight. Additionally, the sidewalls limit fluid connection with the first volume 112 and the ambient external environment of the apparatus 100.

Referring to FIGS. 1A-2, the apparatus 100 may be constructed from the sheet 101 as follows. For ease of description, reference will be made to the "topside" and "underside" of the panels and flaps comprising sheet 101, the "topside" being the portion of the panel or flap visible in FIGS. 1B, 2, while the "underside" is the opposite side not visible in the drawings.

In one example, the apparatus 100 is cut or punched from a single, unitary sheet 101 of suitable material, such as solid bleached sulfate paperboard, plastic, spun nonwoven polymer such as TYVEK® by DuPont, or the like. In another example, the apparatus 100 may be assembled from a plurality of pieces or sheets of suitable material. The material may be an antistatic or static dissipative paper to reduce static deposition of medicine particles on the walls of the apparatus 100. In one example, the sheet 101 may be coated in a static dissipative coating or the like. Inhalation valve 124, exhalation valve 126, and optional viewing window 8 may be first created by adhesively attaching membranes 76, 75, 8 to the appropriate surface of sheet 101 as discussed relative to FIG. 1B. The membranes 76, 75, and 8 may be any suitable material capable of creating a substantially airtight valve or window while also remaining flexible. In one example, the membranes 76, 75, and 8 may be a thin plastic, and polymer, and the like.

The inner housing 120 may be assembled next. The panels and flaps may be fixed or glued together using one or more suitable adhesives. The folding and gluing process starts by applying adhesive to the underside of panel 79A. Panel 79A is folded over so that the adhesive side contacts the underside of bottom panel 2B. Line 87 and the diagonal folds 201A-D, 203A-D run upward and toward the topside of panels 79B, 79C. Adhesive is applied to the underside of flaps 200A-D. Line 87 and lines 204A, B are used to fold panel 96 as a reverse fold to line up the undersides of panels 200A and 200B to the topsides of panels 79A and 79D, respectively. Line 87 and lines 204C, D are used to fold panel 97 as a reverse fold to line up the undersides of panels 200C and 200D to the topsides of panels 79A and 79D, respectively. Panels 79A and 79D are folded along lines 63 and 92, respectively, to bring the topsides of these panels into the corresponding undersides of panels 200A-D. Glue is applied to the topside of panel 79E. Panel 79E is folded along line 94 and glued to the topside of bottom panel 2B.

The outer housing 110 may be assembled around the inner housing 120 next. Adhesive is applied to the underside of panel 79D. The sheet 101 is folded along line 180C so that the undersides of top panel 2 and bottom panel 30 are folded toward one another. The underside of panel 79D is glued to the underside of top panel 30B. Glue is applied, in any appropriate order, to the undersides of panels 47A and 32A. Panel 47A is glued to the topside of panel 47. Panel 32A is glued to the topside of panel 2A. Glue is applied to the underside of panel 71, which is folded along line 57 and glued to the topside of bottom panel 2B over panel 79E.

Figure 3:
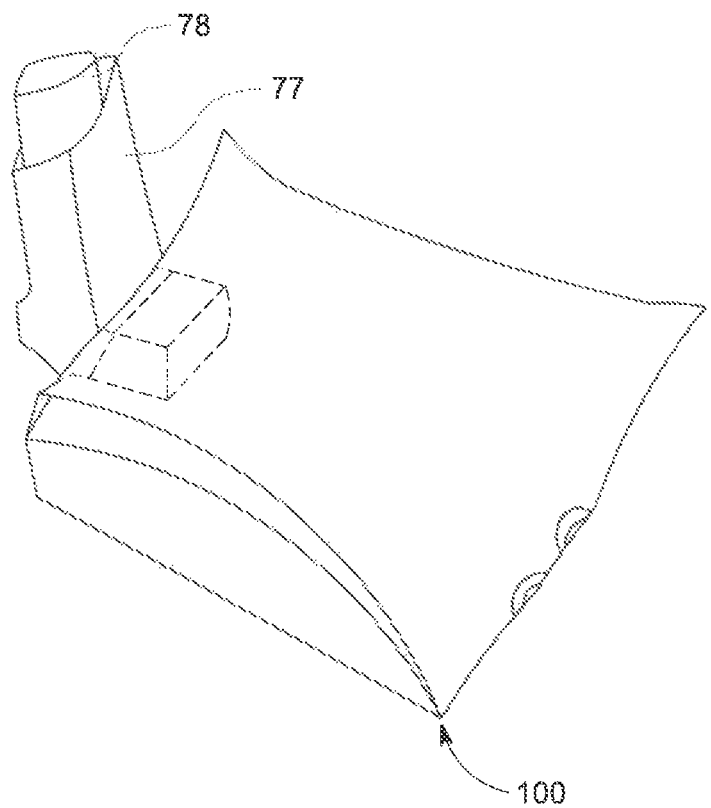
FIG. 3 is a perspective view of the apparatus in an expanded state, in accordance with a first exemplary embodiment of the present disclosure.

FIG. 3 is a perspective view of the apparatus 100 in an expanded state, in accordance with a first exemplary embodiment of the present disclosure. In the expanded state, apparatus 100 is capable of receiving the mouthpiece end of the boot adapter 77 of a conventional inhaler containing an MDI canister 78 inserted through inhaler opening 114 shown in FIG. 1A.

Referring to FIGS. 1A-3, the apparatus 100 may be expanded as follows. When the apparatus 100 is assembled as described above, it is in its flat or collapsed state. If the user presses right side panels 180A and 180B inward toward left side panels 47A and 47B so that they "unfold" along straight, scored fold lines 180C and 47C, respectively, the apparatus 100 pops up into and retains the configuration shown in FIG. 3. The fold lines 63, 87, and 92 allow panels 79B and 79C to be pulled by adhesive and 79D and the rising upper panel 30B upward from their generally horizontal position when apparatus 100 is collapsed so that the panel 79B,C is in a nearly vertical position when apparatus 100 is fully "popped up".

Figure 4:
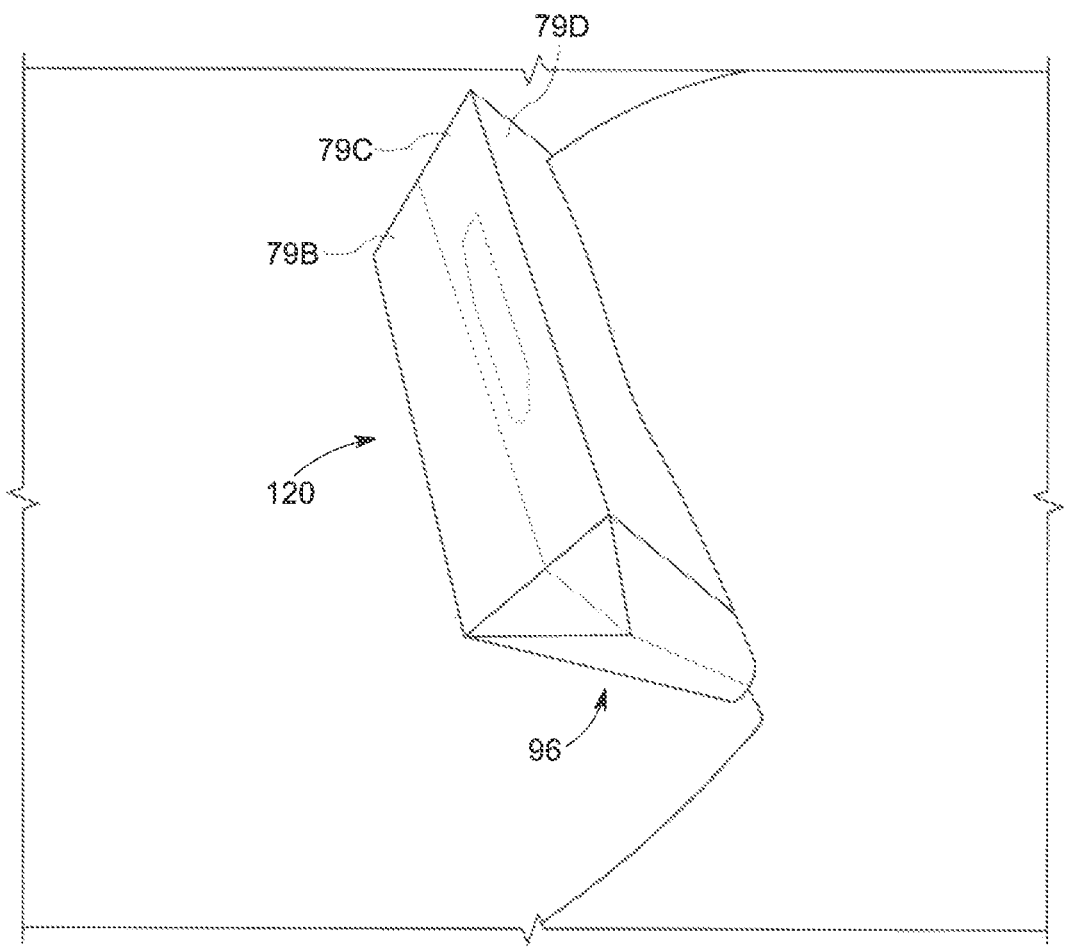
FIG. 4 is a perspective view of the inner housing in an expanded state, in accordance with a first exemplary embodiment of the present disclosure.

Additionally, when the boot adapter 77 with an MDI canister 78 therein is inserted into opening 114, that causes boot adapter panels 32A and 32B to unfold to the maximum extent FIG. 4 is a perspective view of the inner housing 120 in an expanded state, in accordance with a first exemplary embodiment of the present disclosure. In the exemplary embodiment shown in FIG. 4, inner housing 120 is a pyramid connected by panels 79D, 79C, 79B, 96, 97 (not shown), and 79A (not shown). Score line 201A is folded, where score line 203A is not folded, meaning panels 204A and 202A are coplanar, and panel 200A is roughly at a 90° angle with panels 204A and 202A. Panel 97, on the opposite side, has the same configuration. The expanded inner housing 120 may be shaped as any hollow polyhedron connected by panels. In one example, a number of the panels substantially abut portions of the outer housing 110. For instance, the inner housing 120 shown in FIG. 4 may abut the outer housing 110 at panels 96, 97, 79A, and 79D. An inner housing 120 with more sides may abut the outer housing on additional sides.

Referring to FIGS. 1A-4, the inner housing 120 may be expanded as follows. The outer housing 110 of the apparatus 100 is unfolded as described above. As this unfolding occurs, and as right side panels 180A and 180B move inward and engage side panel 97, side panel 97 also is pressed inward. Similarly, as left side panels 47A and 47B move inward and engage side panel 96, side panel 96 also is pressed inward. This causes side panels 96, 97 to fold along fold lines 98, 99 into the configuration shown in FIG. 4. Thus, side panels 96, 97 form a seal with panels 79A-D. Left side panels 47A-B and right side panels 180A-B reinforce the seal by supporting side panels 96 and 97. This effectively reduced or minimizes both inhaled air and exhaled air from bypassing the inhalation valve, substantially increasing the efficiency of the apparatus 100 by reducing or minimizing air inadvertently exhaled (rather than inhaled) by a user during activation of an MDI canister in a boot adapter from being forced around panels 79B and 79C. Additionally, this prevents the inadvertently exhaled air from forcing some of the MDI medication to leak out into the atmosphere between the periphery of opening 114 and the periphery of the MDI boot adapter. The efficiency of the apparatus 100 is thereby increased substantially.

Figure 5:
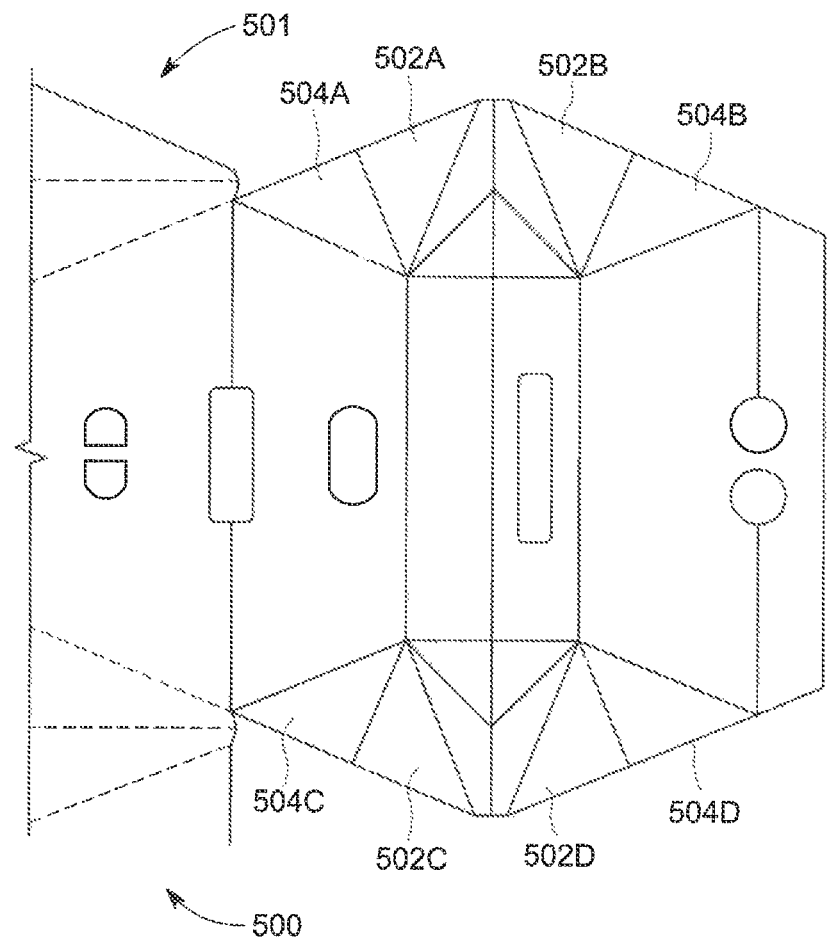
FIG. 5 is a close-up plan view of a sheet from which the apparatus is constructed, in accordance with a second exemplary embodiment of the present disclosure.

FIG. 5 is a close-up plan view of a sheet 501 from which the apparatus 500 is constructed, in accordance with a second exemplary embodiment of the present disclosure. In one example, the design of the sheet 501 may be substantially similar to sheet 101 shown in FIG. 1B, with the exception of additional flaps 502A-D, 504A-D used to form the sides of the inner housing. The additional flaps 502A-D, 504A-D are folded along the score lines shown to create webbed panels of the inner housing. These folded, webbed panels make the inner housing more airtight at the corners of the housing wall when expanded by providing a more robust seal. Other webbed panel designs may be used to provide an airtight seal at the corners of the inner housing.

FIG. 6 is a flowchart 600 describing a method of expanding a medication inhalation apparatus from an initially flat, collapsed state, in accordance with a first embodiment of the present disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 610, an outer housing, an inner housing positioned within the outer housing, wherein the outer housing and the inner housing are substantially airtight when expanded, an inhaler opening formed at least partially within a sidewall of the outer housing at a first location, a mouth opening positioned within a sidewall of the outer housing and the inner housing at a second location, a one-way inhalation valve positioned within a sidewall of the inner housing, and a one-way exhalation valve positioned within a sidewall of the outer housing and the inner housing at a third location are provided in the collapsed state.

In step 620, a pair of opposite sidewall panels on the outer housing is pressed.

In step 630, the outer housing and inner housing are manually expanded to create a first volume encompassed by the outer housing and an inner volume encompassed by the inner housing, wherein the inhaler opening is in fluid communication with the first volume, wherein the mouth opening is in fluid communication with the inner volume, wherein the inhalation valve connects the first volume and the inner volume, wherein the exhalation valve connects the inner volume and the exterior of the outer housing, and wherein gas is flowable from the metered dose inhaler to the first volume, from the first volume to the inner volume, and from the inner volume to the mouth of a user.

Figure 7:
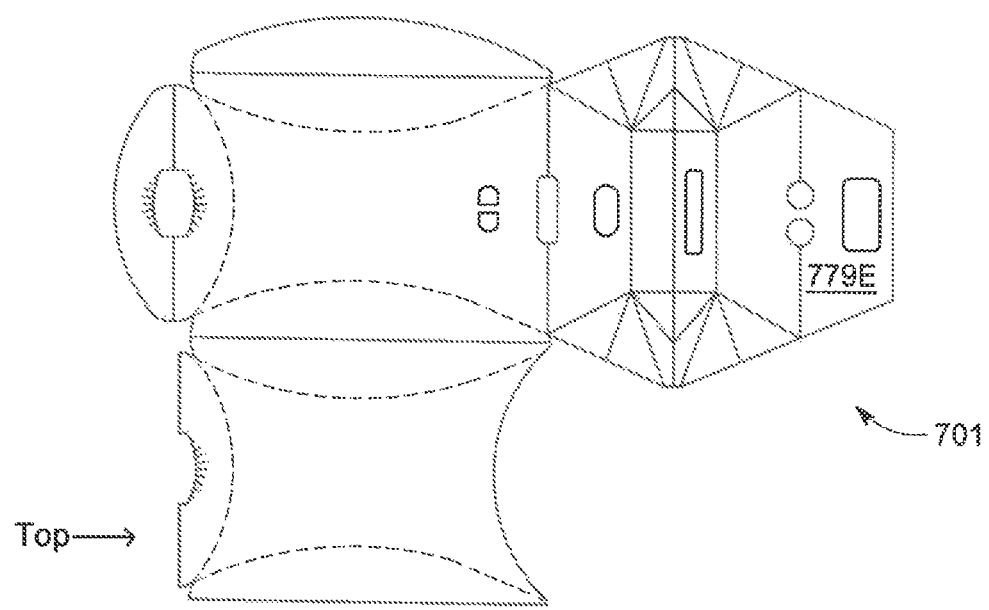
FIG. 7 is a plan view of a sheet from which the apparatus in accordance with a third embodiment of the present disclosure is constructed.

FIG. 7 is a plan view of a sheet 701 from which the apparatus is constructed, in accordance with a third exemplary embodiment of the present disclosure. In this example, the design of the sheet 701 is substantially similar to sheet 101 shown in FIG. 1B, with the additions shown in FIG. 5. However, in this case the front panel 779E for the inner housing, corresponding to panel 79E of the FIG. 2 embodiment, is elongated. Front panel 79E is used to form the mouthpiece, instead of a panel 71 from the outer housing of FIG. 1B, folding to form the mouthpiece. Other than that, the FIG. 7 embodiment is similar to the FIG. 1B embodiment.

Operating Example

The following operating example may illustrate how the apparatus 100 is used in implementation.

The apparatus 100 may be assembled as described relative to FIGS. 1A-2 above. The outer housing 110 may be expanded as described relative to FIG. 3, and the inner housing 120 expanded as described relative to FIG. 4. A user may insert the mouthpiece end of the boot adapter 77 of an inhaler container an MDI canister 78 through the inhaler opening 114 of the apparatus 100 until it fits snugly. The user may place their mouth on the mouth opening 116, and may exhale into the inner housing 120. The user's exhaled breath may exit the inner housing 120 through the exhalation valve 126. Increased pressure in the inner housing 120 may cause membrane 75 to flex away from exhalation valve openings 73, allowing the exhaled breath to escape the apparatus 100. As the user finishes exhaling, the membrane 75 may return to its "closed" position on the apparatus 100, reducing or minimizing the amount of air entering the apparatus 100. The user may next engage the MDI canister 78 to spray medicine into the first volume 112 of the outer housing 110. The medicine may briefly remain in the first volume 112. The user may inhale through the apparatus 100, causing the inhalation valve 124 to open. Membrane 76 may flex into the inner volume 122 of the inner housing 120, allowing the medicine to travel from the first volume 112 to the inner volume 122. As the user continues to inhale, the medicine may continue to travel from the inner volume 122 into the user's mouth through the mouth opening 116. After the user has finished inhaling, the membrane 76 may return to its "closed" position on the inner housing 120, reducing or minimizing the amount of air from the outer housing 110 from entering the inner housing 120.

In some examples, the user may perform some of the steps in a different order. For instance, the user may engage the MDI canister 78 to spray before exhaling, or the user may wait some time between engaging the MDI canister 78 and inhaling. The apparatus 100 is designed to deliver an effective dose even under these conditions.

Test Examples

The following test example may illustrate the effectiveness of the apparatus 100 in creating a medication inhalation apparatus with improved medication delivery.

Three units of the subject apparatus 100, made from 16 pt SBS paperboard, were tested against a Monaghan Aerochamber Z-stat, a non-disposable valved holding chamber. The particle size distributions of the two devices were compared with both coordinated and uncoordinated breathing. Coordinated breathing is defined as actuation of the MDI occurring during the onset of user inhalation. Uncoordinated breathing is defined as actuation of the MDI occurring during the onset of user exhalation. A good metric of the efficacy of the apparatus 100 to mitigate user incoordination is the amount of dose lost from the coordinated breathing test to the uncoordinated breathing test. The Aerochamber unit tested gave a 38% drop in total emitted dose from coordinated to uncoordinated breathing, while the subject apparatus 100 showed, on average, no drop from coordinated to uncoordinated breathing in total emitted dose.

Thus, the invention provides a disposable "pop up", valved apparatus 100 which also allows for natural inhalation and exhalation by a user. The described valved apparatus 100 can be maintained in a collapsed, flat configuration, suitable for storage in a pocket, pocketbook or a briefcase, and expanded just prior to use, after which it can be discarded or re-folded for later use by the same user. The described apparatus 100 may be used by health care workers to demonstrate its use to users needing to receive an aerosol medication from an MDI inhaler. The apparatus 100 also is well suited for use in hospital emergency rooms, health-care clinics, pulmonary function labs, or infirmaries. In addition, its portability and low cost make it ideal for use by relief or world health organizations, especially when aerosol vaccines become available.

While the invention has been described with reference to several particular embodiments thereof, those skilled in the art will be able to make the various modifications to the described embodiments of the invention without departing from the true spirit and scope of the invention. It should be emphasized that the above-described embodiments of the present disclosure, particularly, any "preferred" embodiments, are merely possible examples of implementations, merely set forth for a clear understanding of the principles of the disclosure. It is intended that all elements or steps which are insubstantially different or perform substantially the same function in substantially the same way to achieve the same result as what is claimed are within the scope of the invention. For example, an exhalation valve or other port may be provided on any portion of the inner housing/outer housing. Various other ways of folding the sheet material to achieve the collapsed/expanded configurations can be provided. Different arrangements of lock tabs and lock tab receiving slots than disclosed herein could be provided, or Velcro or similar attachment materials could be used. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A medication inhalation apparatus, comprising:
   an outer housing, collapsible into a substantially flat configuration and expandable to bound a first volume adapted to receive a plume of medication particles ejected by an MDI (metered dose inhaler);
   a fully contained inner housing also collapsible into a substantially flat configuration, located within the outer housing and expandable to bound a second volume;
   a first opening formed through a wall of the outer housing at a first location, in fluid communication with the first volume, and adapted to accommodate a mouthpiece of the MDI;
   second and third openings formed through the wall of the outer housing and a wall of the inner housing, respectively, adapted to form a user mouth opening in fluid communication with the second volume;
   a one-way inhalation valve located within the wall of the inner housing, the inhalation valve connecting the first volume and the second volume;
   side panels extending from the wall of the inner housing, said side panels having diagonal skip-scored fold lines, wherein said side panels form a substantially air tight interface between the first volume and the second volume when the apparatus is in an expanded state; and
   a one-way exhalation valve located within the wall of the outer housing and the wall of the inner housing, the exhalation valve connecting the second volume and the exterior of the outer housing,
   wherein, in the expanded state, gas is flowable from the connected MDI to the first volume, from the first volume to the second volume, and from the second volume to the mouth of the user.

2. The apparatus of claim 1, wherein the outer housing and the inner housing are constructed from a single piece of stock.

3. The apparatus of claim 2, wherein the inner housing is connected to the outer housing at a fold.

4. The apparatus of claim 2, wherein the single piece is sheet stock, and wherein the outer housing and the inner housing are formed by folding the sheet.

5. The apparatus of claim 4, wherein the outer housing is connected to the inner housing adjacent a mouth opening side of the sheet stock.

6. The apparatus of claim 1, wherein the outer housing and the inner housing are at least partially constructed from antistatic material.

7. The apparatus of claim 1, wherein the inner housing has a polyhedron shape, when flattened having at least five sides.

8. The apparatus of claim 7, wherein at least four of the at least five sides abut an interior of the outer housing.

9. The apparatus of claim 1, wherein the inner housing comprises at least two integral side panels.

10. The apparatus of claim 1, wherein the inner housing is formed in part from folded, webbed panels.

11. The apparatus of claim 1, wherein the inhalation valve and exhalation valve are collapsible to a substantially flat configuration.

12. The apparatus of claim 1, wherein the inhalation valve and exhalation valve are operable by the user's inhaling and exhaling.

13. A method of expanding the medication inhalation apparatus of claim 1 from an initially flat, collapsed state, to an expanded state comprising the steps of:
   manually pressing a pair of opposite sidewall panels on the outer housing towards one another, whereby to force the opposite sidewall panels into positions approximately perpendicular to a top and bottom panel of the outer housing; and
   inserting a mouthpiece of the MDI into the first opening in the outer housing.

* * * * *